United States Patent [19]

Curry et al.

[11] 4,259,289
[45] Mar. 31, 1981

[54] APPARATUS FOR RETRIEVING LIQUID SAMPLES FROM TEST TUBES

[75] Inventors: Robert E. Curry, Novato; Michael G. Simonsen, San Rafael; Eric D. Schwartz, Richmond, all of Calif.

[73] Assignee: Bio-Rad Laboratories, Inc., Richmond, Calif.

[21] Appl. No.: 86,916

[22] Filed: Oct. 22, 1979

[51] Int. Cl.³ .................. G01N 1/14; G01N 35/06
[52] U.S. Cl. ........................... 422/64; 73/425.6
[58] Field of Search .............. 422/64, 65, 67; 23/230 R; 141/130; 73/425.6, 423 A

[56] References Cited

U.S. PATENT DOCUMENTS

| | | | |
|---|---|---|---|
| 3,192,968 | 7/1965 | Baruch et al. | 422/64 |
| 3,723,066 | 3/1973 | Moran | 422/64 |
| 3,764,268 | 10/1973 | Kosowsky et al. | 422/64 |
| 3,767,364 | 10/1973 | Ritchie et al. | 422/64 |
| 3,787,185 | 1/1974 | Rohrbaugh et al. | 422/64 |
| 3,788,816 | 1/1974 | Rohrbaugh et al. | 422/64 |
| 3,883,305 | 5/1975 | Hoskins et al. | 422/64 X |

*Primary Examiner*—Ronald Serwin
*Attorney, Agent, or Firm*—Townsend and Townsend

[57] ABSTRACT

Apparatus is disclosed for mixing and then withdrawing a sample of a liquid suspension from a multiplicity of upright vials for subsequent processing of the sample in individual batches. A holder supports the vials in a row and advances them in incremental steps so as to present them at an aspiration station. An aspirator at the station includes a downwardly open suction tube that can be vertically inserted into and withdrawn from the vial. While in the vial, the tube is subjected to a vacuum to withdraw the sample from the vial for flowing it to an instrument. The suction tube is surrounded by a rotary mixer which is activated prior to the withdrawal of the sample to uniformly disperse particles in the liquid. The suction tube and the mixer are generally horizontally movable so that they can be inserted in a container holding a rinsing solution after each withdrawal of a sample liquid from a vial to prevent cross-contamination of the samples. The rinsing solution in the container is drawn into the suction tube and used for purging the previous sample from all conduits.

32 Claims, 8 Drawing Figures

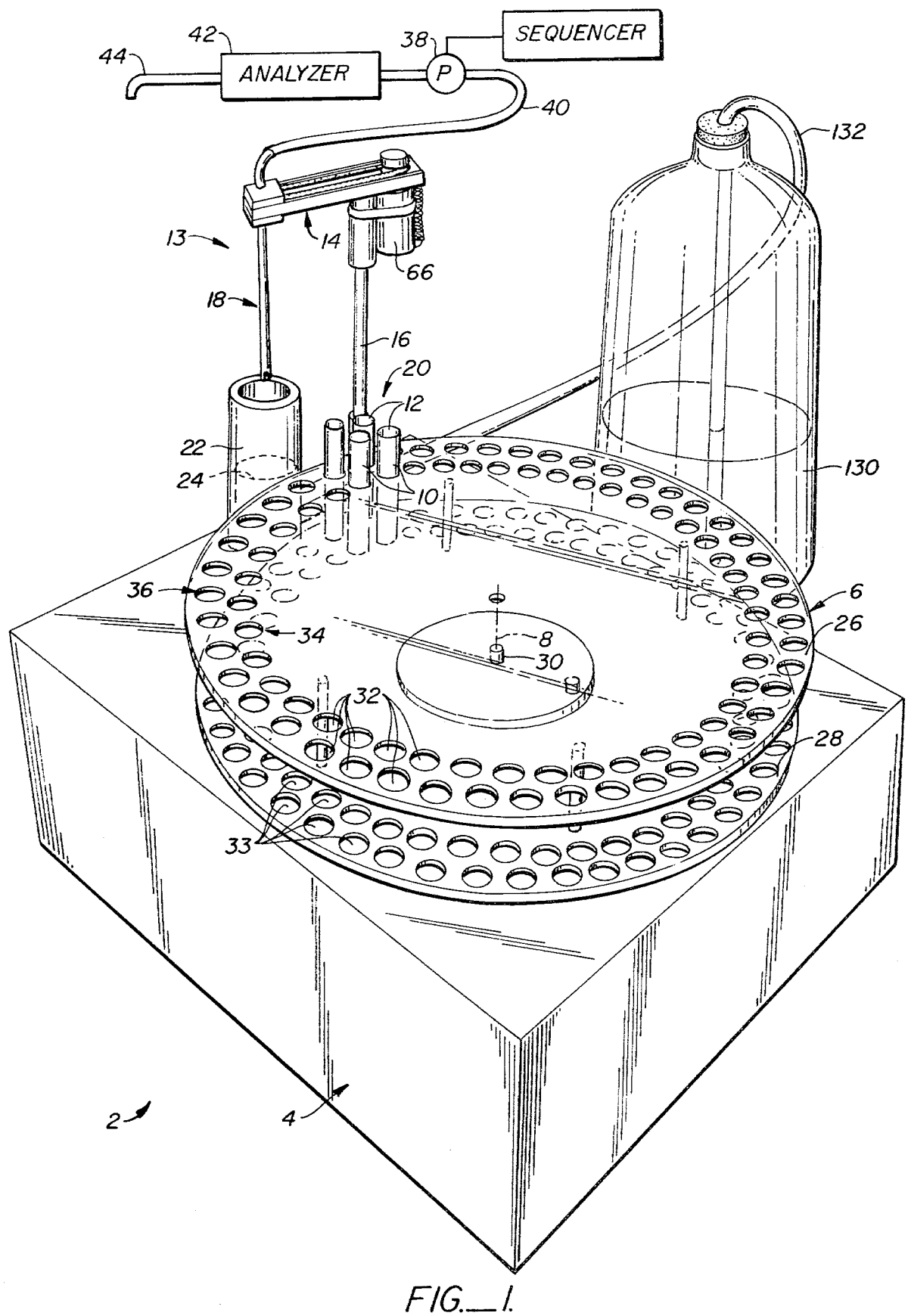
FIG._1.

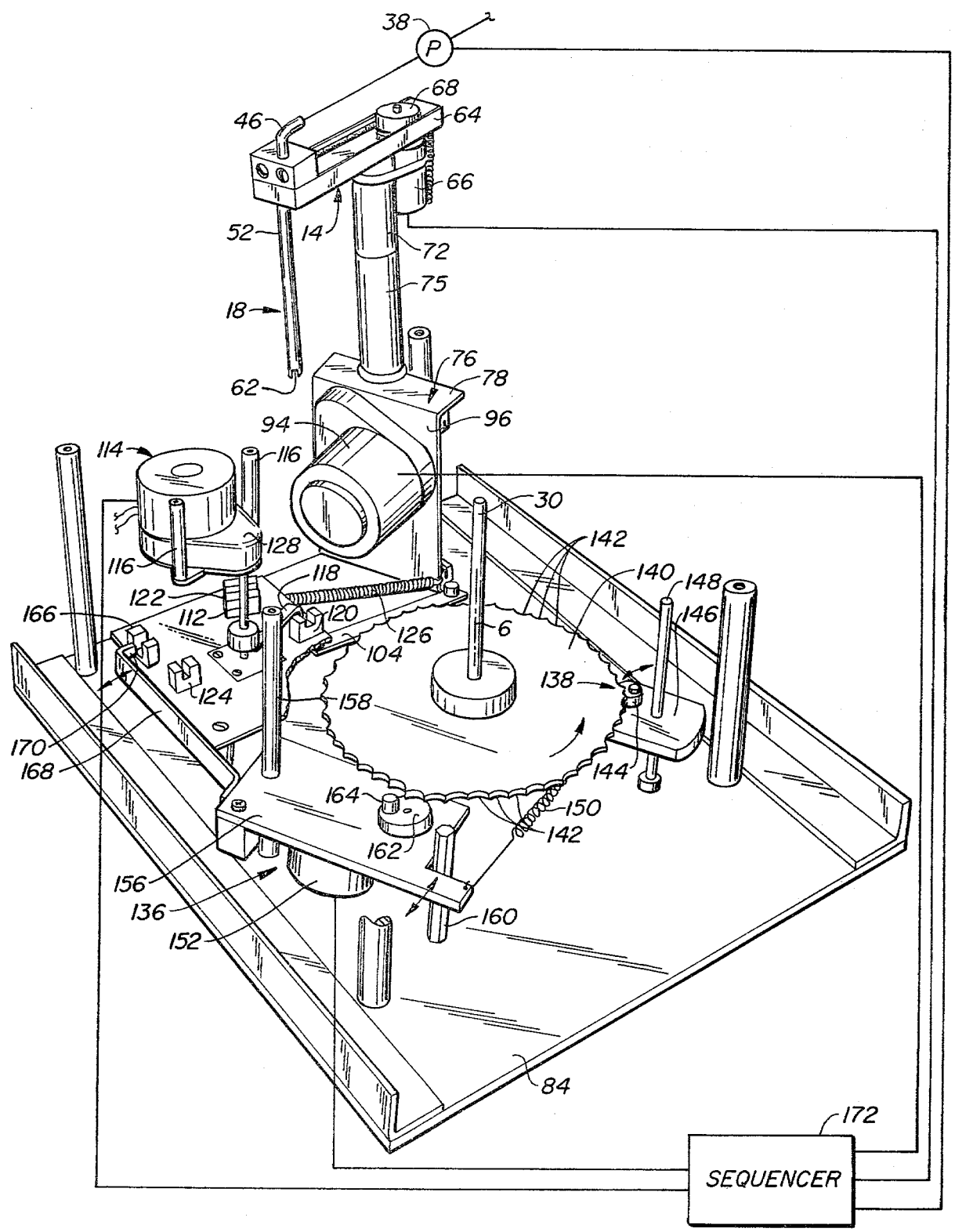
FIG._2.

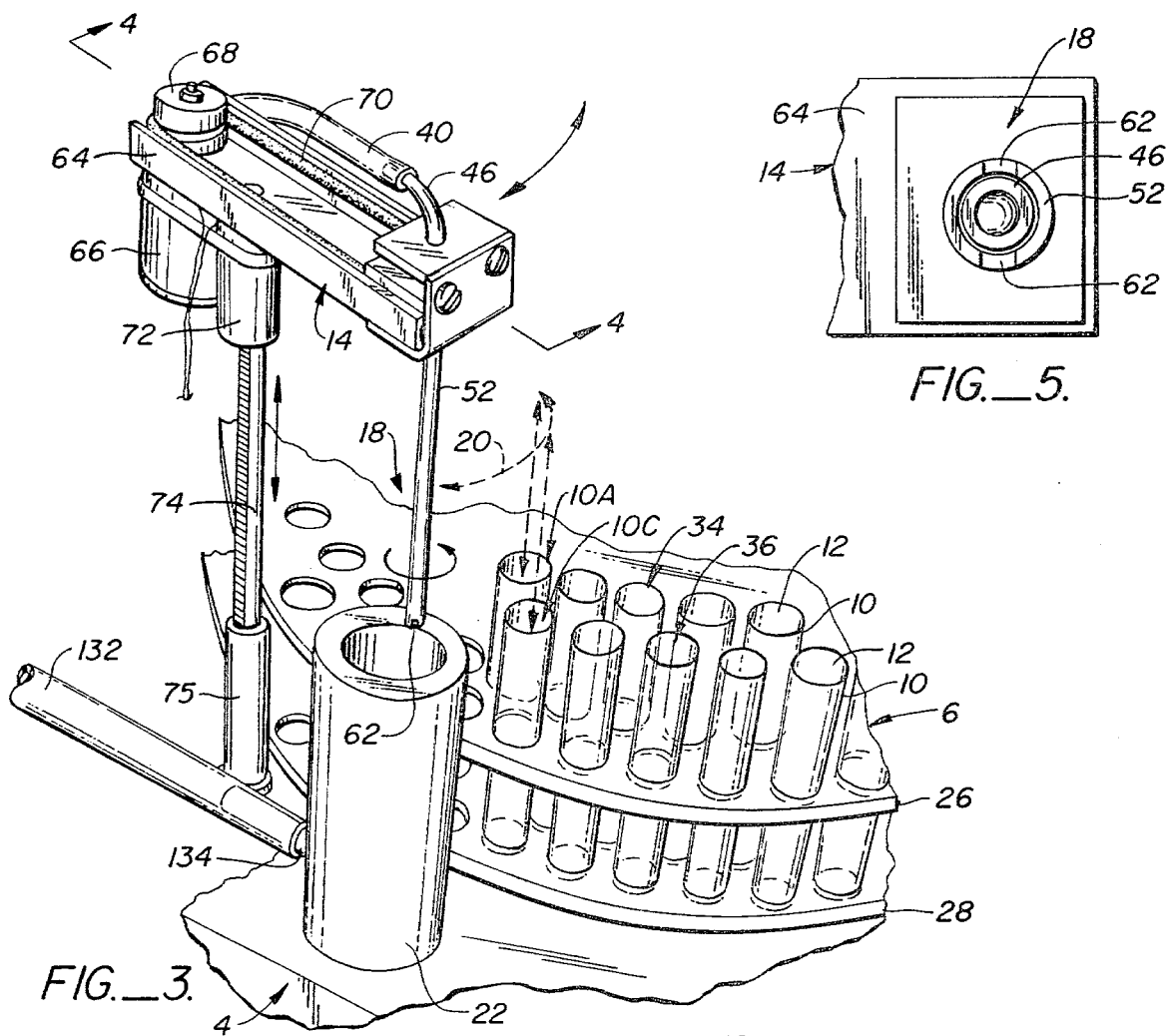
FIG._3.
FIG._5.
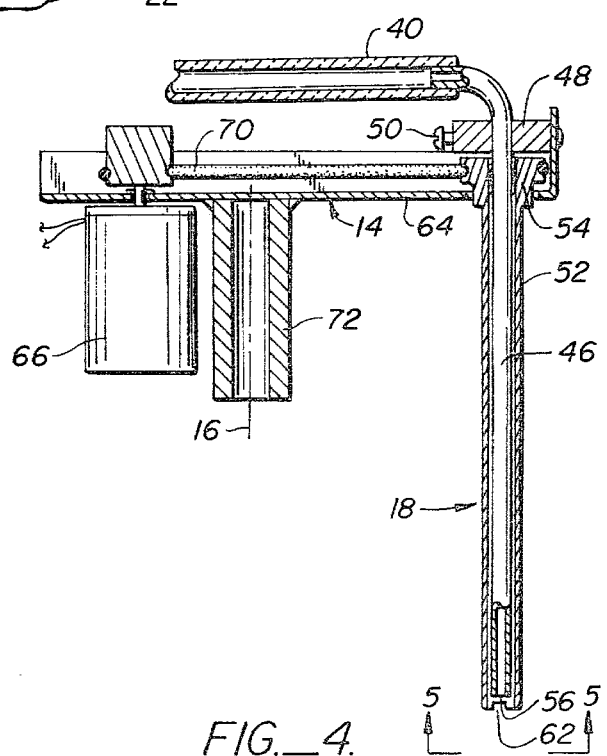
FIG._4.

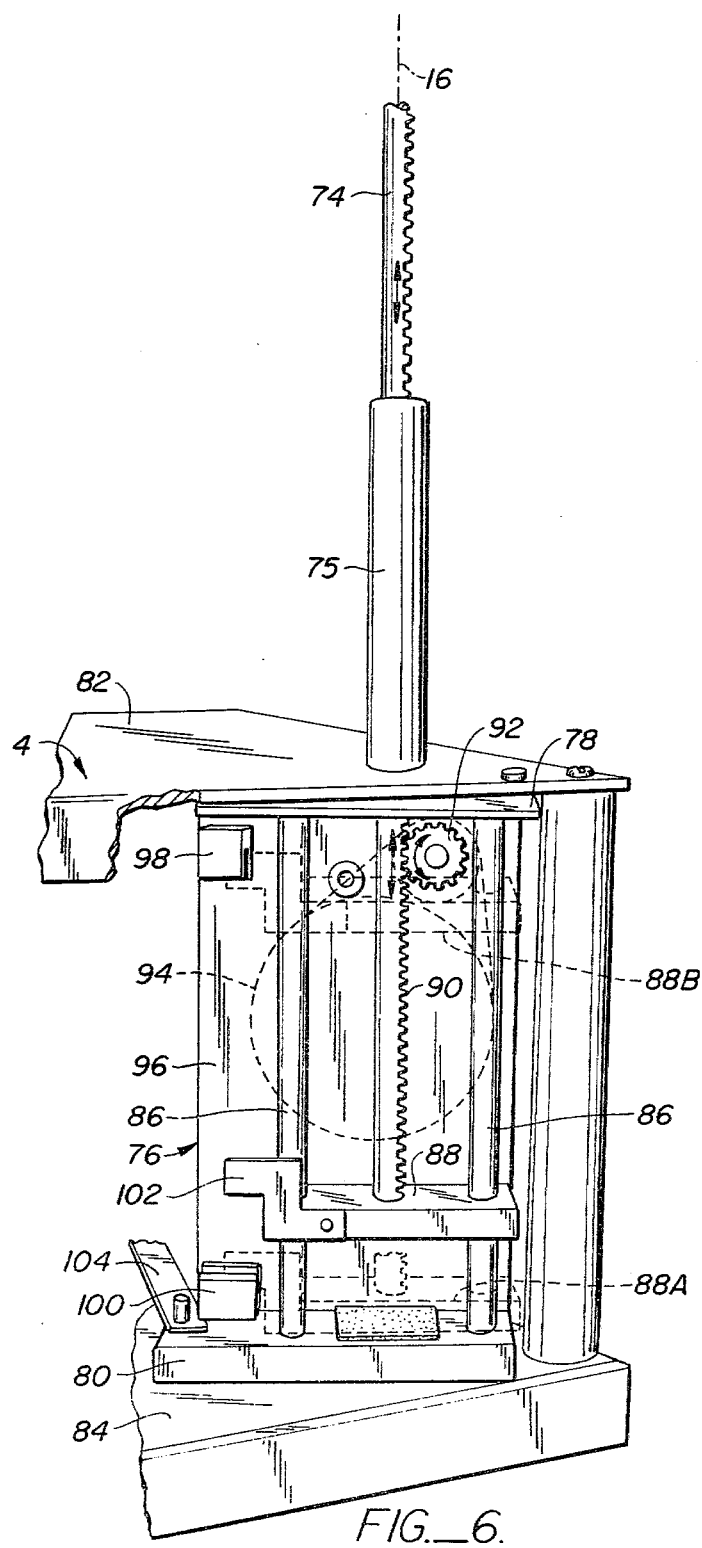
FIG._6.

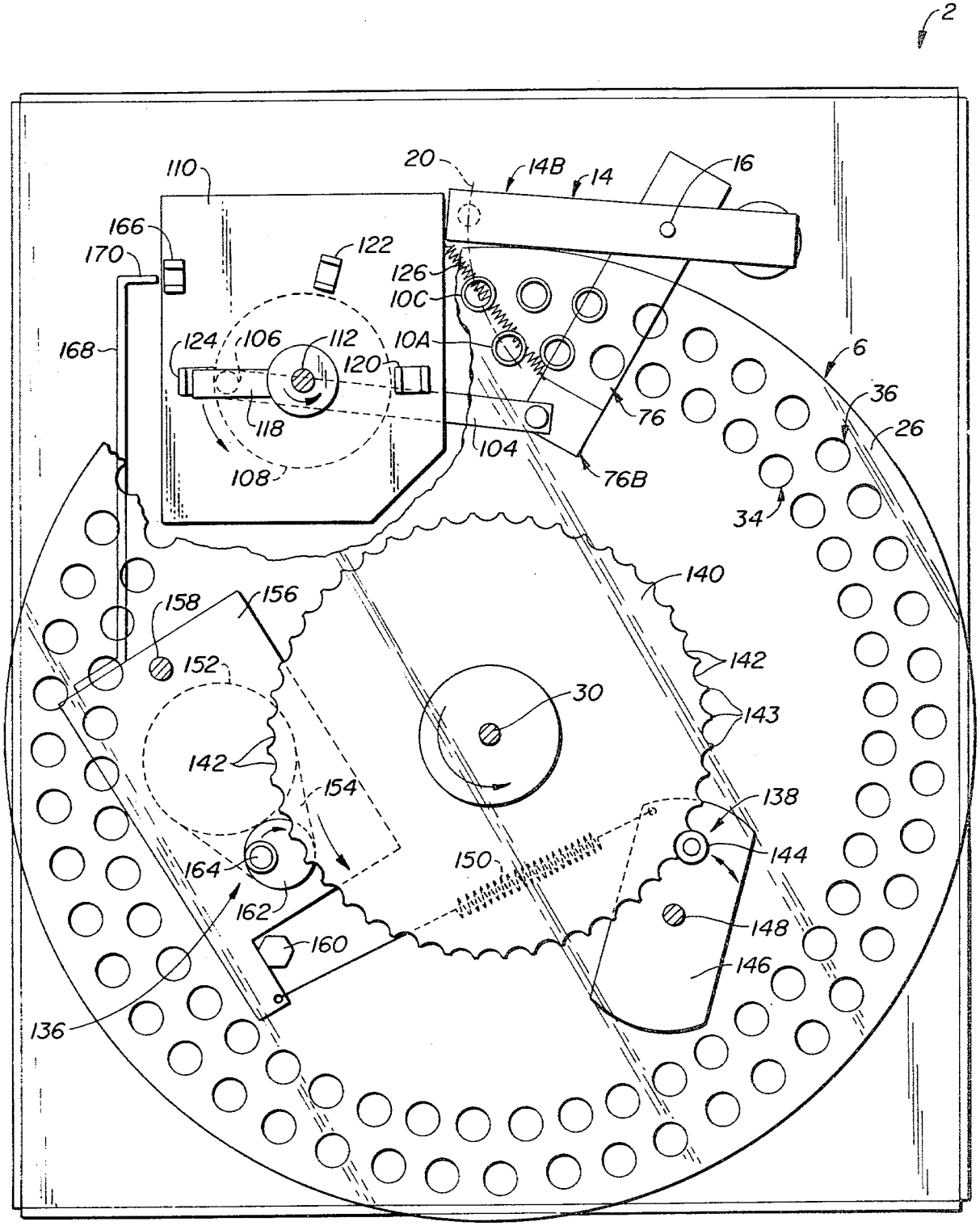
FIG._7.

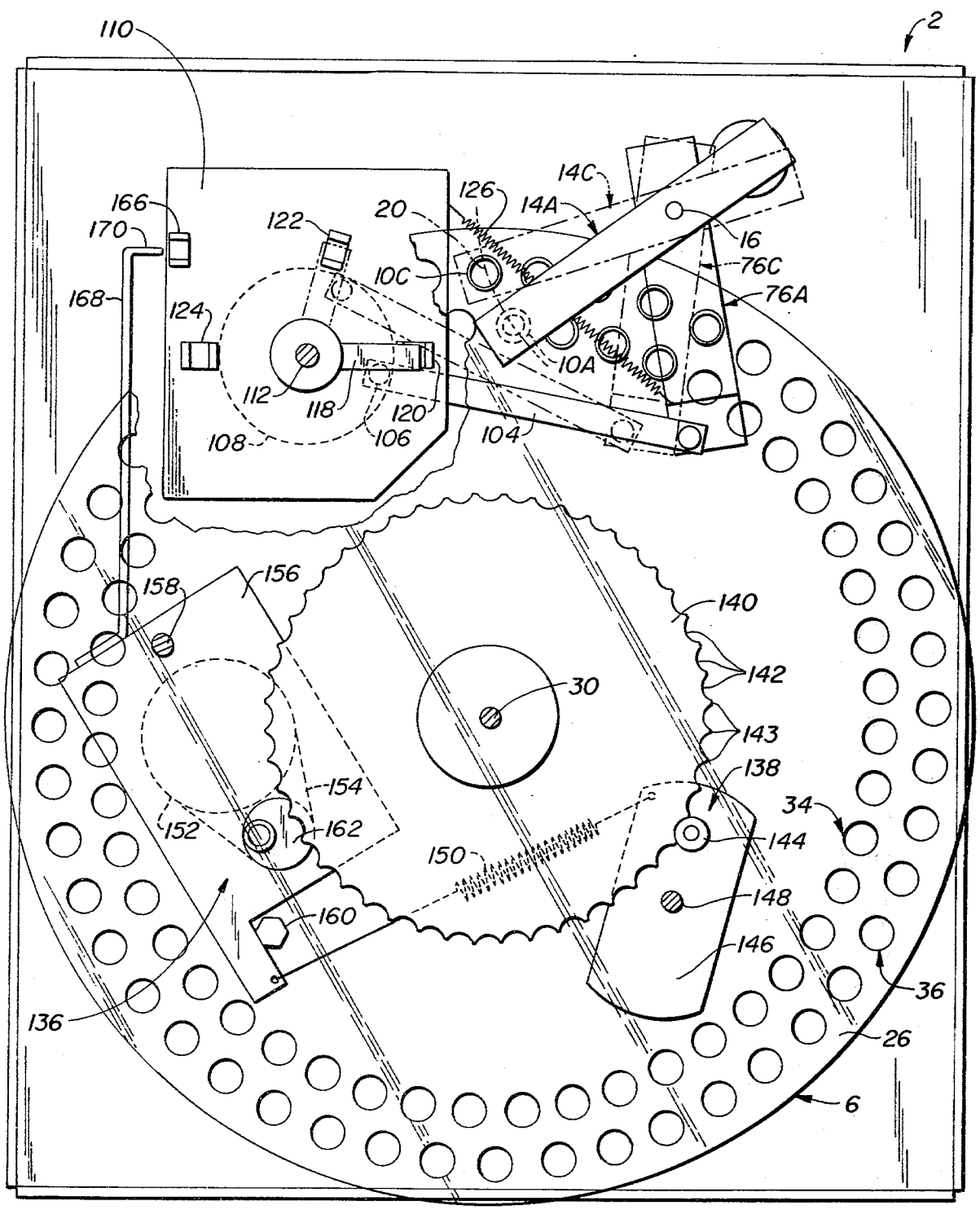
FIG._8.

APPARATUS FOR RETRIEVING LIQUID SAMPLES FROM TEST TUBES

BACKGROUND OF THE INVENTION

The present invention relates to an automated apparatus for retrieving liquid samples such as pretreated blood serum from a multiplicity of sample tubes or vials so that the withdrawn samples can subsequently be tested and analyzed.

There are presently a large number of routine clinical tests, such as blood tests in which fluid samples, e.g. blood samples are placed in a test tube or vial. The samples are appropriately treated, for example to separate the serum from the red blood cells, additives for the tests are added to sample, and thereafter the actual tests are performed, either in the vial or by withdrawing the sample from the vial and testing it outside thereof.

One such test which has recently been developed forms the subject matter of the commonly owned, co-pending U.S. patent application bearing Ser. No. 875,475, filed Feb. 6, 1978 for SOLID PHASE IMMUNAL FLUORESCENT ASSAY METHOD, now U.S. Pat. No. 4,201,763. In that patent application, there is described a fluorescence immunoassay (FIA) for antigens (or haptens) and their antibodies through the use of an immune reactant related to the antibody or antigen to be determined which is covalently bonded or coupled to polymeric particles whose size permits direct measurement of a labeled immunological reagent's fluorescence in an aqueous suspension thereof by direct optical spectroscopy.

Typically, the particles, unknown immune reactant, and appropriate fluorescently labeled immune reactant are mixed under conditions so that a quantity of the labeled immune reactant proportional to the concentration of the unknown immune reactant is immunologically bound, directly or indirectly, to the particles. The particles are then physically separated, usually by centrifuging them, typically at 1500 g to pack the particles at the bottom of the test tube into a pellet. The supernatant is decanted, to the extent necessary the tube or vial is blotted dry and a barbital buffer is added to the pellet in the test tube to reconstitute it and resuspend the particles to form a suspension which includes the fluorescent particles.

The suspension is then analyzed on a fluorometer to determine the concentration of fluorescent particles in the sample to obtain information from which unknown antigen or antibody can be determined.

As has been customery in the past, these tests have heretofore been performed manually one after the other. This required, inter alia, a vigorous manual shaking of the test tube to reconstitute each pellet and resuspend the fluorescent particles. To obtain an accurate test it is, of course, necessary that the suspension be uniform which prolonged the time during which the tube had to be shaken. Thereafter, the sample was fluorometrically analyzed, either in the test tube or by pouring it from the tube into a suitable container of a fluorometer.

This procedure is time-consuming and requires the constant close supervision by a highly skilled technician. More importantly, it gives no assurance that an adequate mixing of the sample has taken place. Without such mixing, however, the ultimate readout is inaccurate and can render the entire test of questionable value. Further, the test is relatively expensive because of the close and constant supervision it requires.

SUMMARY OF THE INVENTION

The present invention seeks to overcome the disadvantages inherent in the prior art procedures for reconstituting the pellets in the bottom of test tubes and especially for uniformly mixing the pellets with the buffer solution and for presenting the resulting suspension to a fluorometer so that it can be appropriately analyzed. The present invention accomplishes this by fully automating both the mixing and the withdrawal of the suspension from the vials so that they can be presented to the appropriate instrument such as a fluorometer.

The apparatus of the present invention is useful and generally applicable to test procedures in which a large number of samples must be tested by removing the sample from the test tube and presenting it to the appropriate instrument and it is particularly advantageous in those instances in which the sample requires intimate mixing preparatory to its testing.

Turning now more specifically to the apparatus of the present invention, it comprises a holder for supporting a multiplicity of vials or test tubes in an upright position in a row and it includes means for advancing the row in incremental steps so as to present the vials at an aspiration station. An aspirator is provided which includes a downwardly open suction tube that can be vertically inserted into and withdrawn from the vial and which, while in the vial, can be subjected to a vacuum to withdraw or aspirate the fluid and flow it via suitable tubing to an instrument where the sample is to be analyzed. In addition to its vertical mobility, the suction tube can be moved in a transverse, generally horizontal direction and a container for a rinsing solution is normally placed proximate the aspiration station and located so that the suction tube can be aligned therewith for immersing the tube in the container after the aspiration of a vial to remove from the tube remnants from the sample in the previously aspirated vial and thereby prevent the cross-contamination of samples. Typically, the vacuum source draws a sufficient volume of the rinsing solution into the suction and hence through associated tubing to purge the entire previous sample before a new one is aspirated from the next vial.

To thoroughly mix the sample before its withdrawal, a mixer is provided which can be inserted in the vial simultaneously with the suction tube. To accomplish this inspite of the usually very restricted vial diameter (typically no more than 12 mm) the suction tube is fixedly attached to an aspirator arm which also rotatably mounts a mixing tube concentrically about the suction tube. The lower end of the mixing tube is serrated or notched to facilitate the agitation of the solution and its uniform mixing. A drive motor is mounted to the aspirator arm and coupled with the mixing tube via suitable belting or the like to rotate the tube when it is disposed in a vial or in the rinsing solution container.

Preferably, the vial holder comprises a tray that is rotatably mounted and on which the vials are loaded in at least one and preferably two or more circular rows which are concentric with the axis or rotation of the tray. The tray includes a notched index plate which is engaged by a cooperating detent biased against the index plate. A vial in each row is aligned with the aspiration station whenever the detent engages a corresponding notch.

The drive for the tray is an intermittent drive that is independent of the positioning index to prevent cumulative positioning errors as would be encountered with gear drive-positioners. Accordingly, it comprises a resilient overdrive which advances the tray so that the detent can engage the next adjacent notch without otherwise affecting the positioning of the vials at the aspiration station.

The aspirator arm is mounted so that it can be pivotally moved about an upright pivot axis whereby the suction tube and the mixer prescribe a circularly arcuate path. The vials at the aspiration station as well as the rinse solution container are positioned along that circular path of the suction tube and mixer so that the latter can be aligned with the former before they are immersed therein. In a preferred embodiment of the invention the rinse solution container is located at one terminal point of the pivotal aspirator arm motion while the vial closest to the axis of rotation of the tray is positioned at the other terminal point of the arm motion. Vials that are in vial rows on the tray radially outward of the innermost row are then located at intermediate points along the circularly arcuate travel path of the suction and mixing tubes. The apparatus includes suitable drive means including locators which arrest the pivotal arm motion whenever the tubes are in alignment with the vial or the container in which they are to be immersed next.

The apparatus further includes a drive, preferably comprising a vertically reciprocating rod, the upper end of which mounts the aspirator arm for raising and lowering the arm together with the mixing and suction tubes so as to immerse the tubes in and withdraw them from the vials at the aspirator station or the container.

To eliminate the need for intricate gearing, which is expensive and requires the utmost precision to avoid cumulative positioning errors, the present invention employs individual and independent drives for each of the motions of the tray and the suction and mixing tubes. Thus, there is an independent drive for advancing, i.e. rotating the tray in increments; for pivoting the aspirator arm to position the tubes; for raising and lowering the tubes to insert and withdraw them from the vials and the rinsing solution container; and for activating the mixer. An appropriate sequencer sequentially energizes the drives so that the operation of the entire apparatus is as follows.

The aspirator has a home or rest position at which the suction tube is aligned with an immersed end in the rinsing solution container. To commence sampling, the tray drive is energized to present the first vial (or vials if there are multiple vial rows on the tray) at the aspirator station. The exact positioning is performed by the index plate and the cooperating detent. Upon the proper positioning or, to save time, even before that the aspirator arm is raised to withdraw the suction and mixing tubes from the rinsing solution and to clear the upper ends of the container and the vials. Thereupon, the aspirator arm is pivotally moved until the tubes are aligned with the vial at the aspirator station in one of the rows, say the radially outermost row. Upon alignment, the aspirator arm is lowered until the lower end of the rotating mixer tube is proximate to but spaced from the bottom of the vial. The mixing tube is now rotated at a relatively high rate to intimately mix the liquid in the tube and to thereby uniformly disperse all particles throughout the liquid.

After completion of the mixing step, typically after about 4 seconds, mixing ceases and the liquid is aspirated from the vial by suction through the suction tube by, for example, energizing a pump. After a sufficient amount of sample has been withdrawn, pumping ceases and the aspirator arm is again raised to clear the upper end of the vials. The arm is now pivoted to return the tubes to the rinsing container where they are immersed, the mixing tube is rotated and rinsing solution is drawn into the suction tube to rinse out all remnants of the sample just withdrawn from a vial. Depending on the construction of the analyzer to which the sample is sent, the rinsing can take place while the sample is being analyzed by discharging the rinsing solution. Frequently, however, the aspiration of rinsing solution from the container does not commence until after the completion of the test on the sample in the analyzer. Thereupon the pump is actuated and rinsing solution is not only flowed through the suction pump but through all corresponding tubing all the way into the analyzer to thereby purge the previous sample and thus prevent the contamination of the next sample.

Thereafter, the mixing and suction tubes are repositioned as above described to align them with a vial in the next, e.g. the radially inward row without again activating the tray advancing drive. The above-summarized steps to mix and withdraw the sample and to rinse the tubes are repeated. After the vial in the last vial row has been aspirated, and usually while the tubes are being rinsed, the tray is advanced by one increment to position the next set of vials at the aspirator station.

From the foregoing, it will be apparent that the apparatus of the present invention provides an entirely automated system for mixing clinical samples before they are tested to provide uniform, homogenous samples and to avoid measurement errors due to incomplete mixing. Further, the apparatus automatically samples the liquid in one vial after the other from the beginning to the end without requiring supervision. This greatly speeds up the testing procedure while freeing highly trained technicians for other than repetitive manual tasks. This not only results in a higher overall test accuracy but also reduces the cost of the tests and thus aids in lowering the otherwise ever increasing cost of clinical tests.

BRIEF DESCRIPTION OF THE DRAWINGS

FIG. 1 is a perspective, overall view of an apparatus constructed in accordance with the present invention for automatically mixing samples in and withdrawing them from a multiplicity of vials;

FIG. 2 is a perspective view similar to FIG. 1 but with all exterior covers removed so as to illustrate the drives employed by the apparatus of the invention;

FIG. 3 is a perspective, enlarged, fragmentary view of an aspirator arm constructed in accordance with the invention and employed on the apparatus illustrated in FIG. 1;

FIG. 4 is a fragmentary, side elevation view, in section of the aspirator arm and is taken on line 4—4 of FIG. 3;

FIG. 5 is a fragmentary end view of the suction tube and the mixer employed by the aspirator of the present invention and is taken on line 5—5 of FIG. 4;

FIG. 6 is a fragmentary, perspective elevation with parts broken away, and illustrates the drive for raising and lowering the aspirator shown in FIG. 3;

FIG. 7 is a fragmentary plan view of the apparatus shown in FIG. 1 with parts broken away and with the cover omitted; and FIG. 8 is a plan view similar to FIG. 7 but illustrates components of the apparatus in differing positions, with some of the positions being superimposed and shown in phantom lines.

DESCRIPTION OF THE PREFERRED EMBODIMENTS

Referring to FIG. 1, a sampler 2 constructed in accordance with the invention generally comprises a case 4, a holder 6 mounted to the case for rotation about an upright axis 8 and holding a multiplicity of clinical test tubes or vials 10 in an upright position so that their open ends 12 face upwardly, and an aspirator 13 mounted to the case for withdrawing liquid samples from the vials. The aspirator includes a generally horizontal aspirator arm 14 that is pivotal about a vertical axis 16 for pivoting an aspirator assembly 18 about axis 16 to align it with vials at an aspiration station 20 or with a rinse container 22 holding a volume of a rinsing solution 24.

In a presently preferred embodiment the rinse container is entirely separate of the case 4 and the vial holder 6 and has a flat bottom so that it can stand on the case. This allows a quick removal of the container for cleaning work on the sampler and the like. By giving the container a relatively larger inner diameter, it is readily repositioned on the case without requiring a precise alignment with the aspiration station since the larger inner diameter compensate for slight alignment errors.

The vial holder comprises a tray defined by a pair of vertically spaced apart discs 26, 28 interconnected by a hub (not separately shown) and fixedly secured to an upright shaft 30 for rotation therewith about upright axis 8. The discs include vertically aligned sets of upper and lower holes 32, 33 which are arranged in an inner and an outer circular row 34, 36 and which are dimensioned so that the vials can be slidably inserted through the upper holes 32 and are engaged and centered by but cannot pass through the lower holes 33 to thereby mount the vials in an upright position. By intermittently rotatably advancing shaft 30 and the discs, the vials are sequentially presented at the aspiration station.

In operation, the vials are filled with a given volume of sample liquid, say 2 ml for 102 mm diameter vials and upon the alignment of one or more vials with the aspiration station, the aspirator arm 14 is pivoted to align the aspirator assembly 18 with a vial. The assembly is thereafter lowered as is discussed in more detail below to immerse it in the sample in the vial, the sample is mixed to form a uniform suspension, and thereafter it is withdrawn by energizing a pump 38 which forms a vacuum in the assembly and draws the sample from the vial via suitable tubing 40 to an analyzer 42 where the sample is analyzed and tested. Since the analyzer forms no part of the present invention, it is not further described herein.

The aspirator 18 is then retracted from the vial and the aspirator arm 14 is pivoted to align the assembly with rinse container 22. The assembly is immersed in the solution and in a preferred embodiment of the invention pump 38 is energized after the previous sample has been tested in analyzer 42 to draw a volume of rinse solution through the assembly, tubing 40 and analyzer 42. As the rinsing solution is drawn in the previous sample is purged from the analyzer and hence discharged via a discharge conduit 44.

Upon the completion of the rinsing step the aspirator assembly 18 is again withdrawn from rinse container 22 and is aligned with the next vial at the aspiration station. The assembly is immersed in the sample in the next vial and pump 38 is energized to draw a fresh sample into the analyzer while the rinsing solution previously flowed into the analyzer is purged therefrom and discharged via conduit 44.

These steps are repeated until all vials on the holder have been aspirated. Thereupon, the vials may be replaced or the holder as a whole may be lifted from case 4 and replaced with another holder filled with vials holding liquid samples to be tested.

Referring to FIGS. 1–6, the aspirator assembly 18 has an elongated, inner tube 46 which is immovably attached with a set screw 50 or the like to a bracket 48 carried by the aspirator arm 14. A mixing tube 52 is concentrically disposed about the suction tube and is carried by a hub 54 rotatably mounted to the aspirator arm so that the rotation of the hub results in a corresponding rotation of the mixing tube.

An open lower end 56 of the mixing tube protudes past the lower end of the suction tube. The lower end of the mixing tube includes a pair of downwardly opening grooves 362 which, when immersed in liquid and when the mixing tube is rotated, significantly enhance the agitation and mixing of the surrounding liquid. The entire assembly has an outermost diameter less than the inner diameter of the vial so that the assembly can be inserted in and retrieved from the vial in a vertical direction while ensureing that the mixing tube can freely rotate. When the diameter of the aspirator assembly is of no concern a flexible sleeve (not shown) may be placed over the outer diameter of the mixing tube. In such an event the sleeve protrudes below the lower end 356 of the mixing tub and the grooves 362 are formed in the sleeve.

The aspirator arm 14 is defined by a channel 64 the forward, i.e. righthand end of which as seen in FIG. 4 mounts the aspirator assembly 18. An electric mixing motor 66 for rotating mixing tube 52 is mounted to the channel adjacent an aft end thereof and includes a grooved pulley 68 over which a drive belt 70 such as an endless resilient rubber ring is slung. The drive belt also engages a corresponding groove in hub 54 so that the motor can rotate the mixing tube and sleeve 60 carried thereon about the upright axis defined by suction tube 46. The arm further includes a vertically oriented, downwardly extending mounting sleeve 72.

A vertically reciprocable rod or post 74 defines pivot axis 16, extends into sleeve 72 and through a guide tube 75 that projects from case 4 into the interior of the case where it is carried by a movable frame 76 disposed within the case. The rod has an axially extending flat face which carries a gear rack 90 for purposes further described below. The interior of sleeve 72 has a corresponding radially inwardly projecting protrusion (not shown) for engaging the flat face of the rod to prevent relative rotational movements between the aspirator 13 and the rod while permitting the ready removal of the aspirator from the rod by slipping the former in a vertical direction off the latter.

The movable frame has a generally U-shaped configuration with upper and lower flanges 78, 80 disposed proximate a housing 82 and a base 84, respectively, of case 4. The lower end of the guidance tube is affixed to the upper flange 78 and protrudes through a hole formed in the case housing. The lower flange 80 of the frame receives an aligned shaft (not separately shown) which protrudes through a correspondingly positioned hole in the base 84, so that the frame 76 and therewith guide tube 75 can be pivoted about upright axis 16 for purposes further described below.

A pair of spaced apart, parallel and vertical guide posts 86 are affixed to the upper and lower flanges 78, 80 of the frame and they straddle guide tube 75. A yoke 88 has holes formed to slidably engage the guide posts so that the yoke can move vertically along the posts from a lower position 88A to an upper position 88B, both of which are shown in phantom lines in FIG. 6.

The lower end of upright rod 74 is affixed to yoke 88 and its gear rack 90 meshes with a pinion gear 92 driven by a reversible electric motor 84 attached to the back side of frame web 96 facing away from the vertical guide posts.

Upper and lower position transducers such as optical sensors 98, 100 are attached to the frame, e.g. to frame web 96 and they cooperate with an indicator 102 attached to yoke 88 so as to generate upper and lower position signals when the yoke is in its raised or lowered positions. Signals from the sensors are used to de-energize motor 94 when the yoke and therewith upright rod 74 reach these positions.

Preferably, motor 94 is a load reversing motor, i.e. a motor which reverses its direction of rotation upon encountering a predetermined torque on its shaft to prevent damage to the motor or the associated gearing should either of the optical sensors fail or if an excessive load is applied to the upright rod due to an interference between the aspirator 13 and any of the vials 10, rinse container 22 or other hardware.

Referring now to FIGS. 2, 3 and 6–8, movable frame 76 and therewith upright rod 74 are also pivotable about axis 16. The pivotable frame motion is imparted to the aspirator arm 14 by virtue of the engagement of the upper end of post 74 with mounting sleeve 72.

Pivotable motion is imparted to the frame 76 by a crank arm 104, the respective ends of which are pivotally attached to a lower flange 80 of the movable frame and to a crank pin 106 eccentrically mounted to a crank wheel 108 disposed between base 84 and a platform 110 vertically spaced therefrom. An upright shaft 112 to which the crank wheel is mounted protrudes through the platform and is driven by a motor 114 mounted to the underside of housing 82 with spaced apart mounting bolts 116.

An indicator arm 118 rotates with shaft 112 and is positioned to interrupt three optical sensors 120, 122 and 124 during one full rotation of the crank wheel to generate three position signals. The three signals are used to de-engerize motor 114 to terminate its rotation when the movable frame 76 and therewith aspirator assembly 18 are at predetermined locations as is further discussed below. A tension spring 126 biased the movable frame in a clockwise direction to take up play and prevent backlash in the pivoting mechanism.

When motor 114 is energized it rotates shaft 112 via gearing 128 and therewith crank wheel 108 and indicator arm 118. Rotation of the crank wheel is transmitted to the frame via crank arm 104 to pivot the frame between terminal positions 76A (shown in FIG. 8) and 76B (shown in FIG. 7). The pivotal frame movement is duplicated by aspirator 13 and places the aspirator arm 14 in terminal positions 14A (FIG. 8) and 14B (FIG. 7). The two terminal positions coincide with the alignment of indicator arm 118 with optical sensors 120 and 124, respectively. The aspirator arm 14, movable frame 76, crank arm 104 and crank wheel 108 are sized so that when the frame is in position 76A (FIG. 8) the aspirator arm vertically aligns the aspirator assembly 18 with a vial at position 10A (FIG. 8) in the inner vial row 34 at the aspiration station 20.

It should be noted that the aspiration station is defined by a circularly arcuate line the origin of which is vertical axis 16. The line has a radius equal to the distance between this vertical axis and the axis of the aspirator assembly so that the aspirator assembly can be vertically aligned with any point on this line.

The second terminal point 76B of the pivotal frame 76 is chosen so that it vertically aligns the aspirator assembly with rinse container 22 when the aspirator arm is at position 14B (FIG. 7). In that position, indicator 118 is aligned with optical sensor 124 to generate a position signal which indicates the alignment of the mixing-withdrawal assembly with the rinse container.

A third, intermediate position 76C of the movable frame (FIG. 8) is determined by optical sensor 122. When the indicator 118 is aligned with sensor 122 aspirator arm 14 is at position 14C (FIG. 8) and the aspirator assembly is aligned with a vial at position 10C in outer vial row 36 at aspiration station 20.

From the foregoing, it will be apparent that the relative position of the vial receiving holes 33, 34 in discs 26, 28 should be carefully chosen to minimize motion and indexing of the vial holder 6 as is further discussed below. Accordingly, the vial holes are arranged so that two holes are simultaneously aligned with aspiration station 20 or, expressed in other words, so that two holes, one in each of rows 34 and 36 lie on a circularly arcuate line, the origin of which is vertical axis 16 and the radius of which equals the distance between this axis and the center of the aspirator assembly. When so positioned, two vials, one in each row can be aspirated before the vial holder 6 must be advanced to present the next set of two vials at the aspiration station.

Referring now to all figures, the manner in which the aspirator assembly 18 is moved to sequentially aspirate the vials at the mixing station should be apparent. To briefly summarize, movable frame 76 has a home position 76A at which the aspirator assembly is aligned with rinse container 22. To initiate the aspiration of liquid samples from vials at the aspiration station 20, motor 94 raised upright rod 74 and therewith aspirator arm 14 and aspirator assembly 18 until the lower end of mixing sleeve 60 clears the upper edges of both the rinse container and the vials. At that point motor 94 is de-energized.

Motor 114 is now activated to rotate crank wheel 108 until indicator 118 interrupts optical sensor 120 and the frame is at position 76A (FIG. 8) to vertically align the aspirator assembly with the vial at position 10A on inner vial row 34. The interruption of sensor 120 de-energizes motor 114 and thereby arrests the pivotal motion of frame 76. Vertical position motor 94 now lowers rod 74 and therewith the aspirator assembly until the lower end of mixing sleeve 60 is proximate but slightly spaced above the bottom of the vial. This position is determined when indicator 102 interrupts the lower optical sensor 100 mounted to frame 76.

Mixing motor 66 is now energized to rotate sleeve 60 at a relatively high rate, say rpm for the necessary time to uniformly disperse all particles in the liquid sample and form a homogenous suspension. For dissolving centrifuged pellets and suspending them in the liquid a mixing time of 4 seconds is normally sufficient. Upon completion of the mixing, pump 38 is activated to withdraw the desired sample volume by suction through suction tube 46 and flow it to analyzer 42. The pump is de-energized as soon as the necessary volume has been withdrawn from the vial.

While the sample is being analyzed, vertical position motor 94 raises the aspirator assembly 18 end motor 114 rotates crank wheel 108 in a counterclockwise direction (as seen in FIG. 8) until indicator arm 118 interrupts sensor 124. It will be noted that the indicator arm passes through optical sensor 122 and suitable logic (not separately shown) is provided to override the position signal generated by sensor 122 and to continue the operation of motor 114 until the indicator is at sensor 124. The aspirator assembly is now lowered to immerse it in the rinsing solution in container 22.

Assuming that rinsing solution is utilized to purge the previous sample from analyzer 42, after completion of the analysis of the previous sample, pump 38 draws rinsing solution by suction from container 22 into tubing 40 and hence analyzer 42 to purge the previous sample and at the same time thoroughly rinse all components that came into contact with the previous sample. A cross-contamination of the next sample is thereby prevented.

As rinsing solution is withdrawn from the container, it is refurbished with fresh rinsing solution from a reservoir such as a bottle 130 fluidly connected with the container via tubing 132 and an intake pipe 134 at the bottom of the container so that the rinsing solution level in the container corresponds to the solution level in the bottle.

Returning to the operation of aspirator assembly 18, it is preferred that mixing motor 66 be energized during the rinsing step to facilitate the rinsing of all remnants of the earlier sample. Upon completion of the rinsing step pump 38 is de-energized and the vertical position motor 94 returns the aspirator assembly into its raised position. Thereupon motor 114 pivots frame 76 into its intermediate position 76C until indicator arm 118 interrupts optical sensor 122. Aspirator arm is at intermediate position 14C and aspirator assembly 18 is aligned with the vial at position 10C in outer row 36. The position signal generated by optical sensor 120 as the indicator arm passes it is suppressed so that the motor remains energized until the indicator arm reaches sensor 122.

The aspirator assembly is now lowered, and the sample in tube 10C is mixed and withdrawn. Thereafter, the aspirator assembly is returned to rinse container 22 and this sample is also purged from all conduits and the analyzer in the manner described above.

With the aspiration of the vial at 10C the samples in all vials at the aspiration station 20 have been tested. Vial holder 6 is now advanced to present the next set of two vials at the station. This is accomplished by means of a tray advancing drive 136 and a tray index 138 best illustrated in FIGS. 2, 7 and 8.

To facilitate the illustration, housing 82 is not shown in FIGS. 7 and 8. However, the vial holder disc 26 is superimposed over the illustrations in FIGS. 7 and 8 so as to pictorially show the interrelationship between the vial positions 10A and 10C at the aspiration station 20 and the vial holder drive and index.

Referring now to FIGS. 2, 7 and 8, the gray index 138 is defined by a circular index plate 140, the periphery of which is scalloped and defines a number of preferably circularly concave index notches 142 which equal in number the number of vial holes in row 34. For a two-row disc, the number of notches equals the total number of vial positions on the disc divided by the number of vial rows or, in the illustrated instance, divided by two. A detent wheel 144 such as a roller bearing is mounted to the upwardly facing side of a plate 146 disposed beneath the index plate and pivotally mounted to an upright post 148 extending from the base 84 to the case housing (not shown in FIGS. 2, 7 and 8). One end of a tension spring 150 is anchored in plate 146 and biases it in a counterclockwise direction as is viewed in FIGS. 7 and 8. The spring thereby biases the convex periphery of the detent wheel 144 towards the index plate 140 and nests the index wheel in a notch. If the two are misaligned, the force from the spring rotatably moves the index plate until the detent wheel fully nests in the notch.

The index plate is affixed to shaft 30 mounting vial holder 6 so that it rotates therewith an it is oriented so that when the detent wheel nests in an index notch 142 a corresponding set of two vial holes in the inner and outer vial rows 34, 36 is at positions 10A and 10C and aligned with aspiration station 20. The tray index 138 permits the rotation of both the vial holder 6 and the index plate 140 by correspondingly pivoting the detent plate 146 about post 148. However, the detent wheel will always come to rest in an index notch and a pair of vial holes will, therefore, always be aligned with the aspiration station.

The tray advancing drive 136 comprises a tray drive motor 152 which includes gearing 154 and which is mounted to the underside of a mounting plate 156 that is pivotable about a post 158 extending between base 84 and housing 82 (not shown in FIGS. 2, 7 and 8). One end of tension spring 150 engages the mounting plate and biases it in a counterclockwise direction, as seen in FIGS. 7 and 8. A stop 160 in the form of another post extending between the base and the housing limits the extent to which the tension spring can pivot the mounting plate.

The tray drive motor 152 drives a crank wheel 162 disposed on the upwardly facing side of the mounting plate and fitted with an eccentrically mounted roller bearing 164 which forms a drive pin for the disc plate 140. The crank wheel and the drive pin are positioned so that when the wheel is rotated through one full revolution, the drive pin engages one of the index plate notches 142 and advances it a sufficient distance so that detent wheel 144 engages the next index notch 142. Typically, the drive pin will advance the index plate by more than one-half the spacing between two adjoining index notches 142 and less than one and a half such spaces to prevent an advance of the index plate 140 by more than one notch.

As the crank wheel and the drive pin are rotated, preferably in a clockwise direction as indicated by the arrow in FIG. 7 and the pin engages an index notch 142, mounting plate 156 is pivoted in a clockwise direction against the force exerted by tension spring 150 to assure a firm engagement of the index notch by the drive pin while avoiding the need for precise dimensional alignments between the drive pin and the index wheel which would otherwise be necessary. Stop 160 prevents a continuous engagement of the drive pin with the index notches, which could result in an overtravel of the index plate, by limiting the extent to which the mounting plate 156 and therewith the drive pin can pivot towards the index plate so that through part of a full rotation of crank wheel 162 the drive pin is disengaged from the index plate.

The pivotal motion of the mounting plate when the crank wheel 162 goes through one full revolution is utilized to de-energize the tray drive motor 152. For this purpose, an optical sensor 166 is mounted to platform 110 and an elongated index arm 168 is affixed to mounting plate 156 and dimensioned so that a pointer 170 of the index arm is normally clear of optical sensor 166 but interrupts it when the mounting plate pivots due to the rotating motion of the drive pin. The resulting signal is used to de-energize the drive motor. Since the signal is generated while the drive pin engages a notch, the de-energization of motor 152 is sufficiently delayed to permit the motor to rotate the crank wheel 162 until the wheel has completed one full revolution and has returned the drive pin to its home position, for example, the position illustrated in FIG. 7.

Turning now to the overall operation of the sampler 2 and referring to all drawings, holder 6 is initially loaded by placing sample holding vials 10 in the corresponding vial holes 32, 33 in discs 26, 28 of the holder. At this point, two vials will be at vial positions 10A, 10C in alignment with aspiration station 20 while aspirator assembly 18 is at aspirator arm position 14B and immersed in rinse container 22.

A sequencer or timer 172, which may be a mechanical, electromechanical or electronic sequencer, or a combination of two or more of these, is provided to energize electric motors 66, 94, 114 and 152 as well as pump 38 at the appropriate times in the operating cycle of the sampler of the present invention. Of course, the motors may also be activated manually should that be desired. If the sampler is coupled with analyzer 42 synchronizatin with the analyzer is further provided. Since this synchronization forms no part of the present invention, it is not discussed herein in detail. Further, the construction of sequencers of the type employed here is well-known by those skilled in the art and is, therefore, not set forth in detail.

Functionally, the sequencer first energizes vertical position motor 94 to raise the aspirator assembly 18 until a signal from upper sensor 98 on movable frame 76 indicates that the assembly is in its raised position. The signal is used to de-energize motor 94. The sequencer on its own or by means of the signal received from the upper sensor now energizes motor 114 to pivot aspirator arm 14 until the aspirator assembly is aligned with the vial at position 10A. Upon arrival of the aspirator assembly at that location, optical sensor 120 generates an output signal which is used to de-energize motor 114 and which can also be sued by the sequencer for energizing the vertical position motor 94 to lower the aspirator assembly. When the assembly is in its lower position the lower optical sensor 100 on movable frame 76 generates a corresponding signal which is used to de-energize position motor 94 and which can be employed by the sequencer to energize motor 66 to rotate mixing sleeve 60 for the required time period. Mixing motor 66 is de-energized after the preset time has elapsed, at which point sequencer 172 energizes pump 38 to withdraw the desired sample volume from the vial. De-energization of the pump is again accomplished after a preset time period has elapsed or after a predetermined sample volume has been withdrawn, whichever is appropriate in a given case.

Next, the sequencer sequentially energizes vertical position motor 94, pivot motor 114, the vertical position motor and the mixer motor to raise the aspirator assembly, pivot it into its rinsing position 14B lower it to submerge it in rinsing solution in container 22 and to thereafter rotate mixing sleeve 60. Depending upon the interrelationship between the analyzer 42 and sampler 2 of the present invention, the sequencer energizes pump 38 after completion of the analysis of the sample previously withdrawn from the vial at position 10A to purge all sample remnants from suction tube 46, tubing 40 and analyzer 42. In this event the sequencer is responsive to the analyzer and does not commence the withdrawal of rinsing solution from container 22 until the completion of the analysis of the previous sample. Alternatively, if the analyzer is not purged with rinsing solution from container then the rinsing of the suction tube and tubing 40 can commence as soon as the aspirator assembly is immersed in the rinsing solution. Preferably, rotation of the mixing sleeve 60 continues while the rinsing solution is withdrawn from the container but may cease for commencement of the withdrawal or during the withdrawal of the rinsing solution if that is considered advantageous.

Upon the completion of the rinsing step the sequencer de-energizes pump 38 and repeats the above-described steps to immerse the aspirator assembly in the vial at position 10C to withdraw a fresh sample from that vial. After the withdrawal of the sample the aspirator assembly is returned to the rinsing container for rinsing and purging all sample remnants.

As soon as the aspirator assembly has been retracted from the vial at location 10C, or while the assembly is immersed in the container 22, the sequencer energizes tray drive motor 152 to advance index plate 140 by one notch. As crank wheel 162 rotates mounting plate 156 pivots in a clockwise direction while drive pin 164 rotatably advances the index plate 140. This advance dislodges detent wheel 144 from the notch it previously engaged and thereby pivots detent plate 146 in a clockwise direction as the detent wheel rolls over the ridge 143 between adjoining notches. Spring 150 biases the detent wheel into the next adjoining notch. At about that point, drive pin 164 becomes disengaged from the notches and further advance of the index plate ceases. With the engagement of the next notch by the spring-loaded detent wheel, the next set of vials is at positions 10A and 10C and aligned with the aspiration station.

The pivotal motion of mounting plate 156 is transmitted to index arm 168 and moves pointer 170 into registration with optical sensor 166, thereby signaling that the vial holder has been advanced to present the next set of vials at the aspiration station. The output of sensor of 166 is used to de-energize tray drive motor 152 with the appropriate time delay to permit drive pin 164 to complete one full revolution and to return to its home position.

It will also be noted that the exact alignment of the next set of vials with the aspiration station is accomplished by detent wheel 144 and not by drive pin 164 so that there is considerable latitude for the drive pin to under or overtravel so long as it is assured that the detent wheel in fact rides over the ridge 143 between the notch it previously engaged and the adjoining notch and so long as the drive pin does not advance the index plate by so much that the index wheel rides over an additional ridge and comes to reset in the following notch.

The aspiration of samples from the new set of vials at the aspiration station now continues in the above-described manner, all steps being repeated until samples have been withdrawn from all vials on holder 6.

As suitable indicator such as a magnetic switch (not separately shown) can be provided which is activated by a magnet in a "last vial" on the holder (not shown) to generate a signal that can be used to deactivate the further operation of the sampler of the invention until vials with fresh samples have been placed in the holder. To speed up the replacement of vials the discs 26, 28 of the vial holder can be constructed as a unit that can be lifted off shaft 30 and replaced with another unit already filled with the next set of vials to enable a substantially continuous operation of the sampler and to minimize downtimes.

We claim:

1. Apparatus for sequentially aspirating a liquid from a plurality of upwardly open vials for the subsequent individual processing of aspirated liquid from each vial comprising: an aspirator including an upright, downwardly opening suction tube for sequential insertion into the vials; tray means supporting the vials for incrementally moving the vials to an aspiration station; positioning means for aligning the suction tube and the vial at the aspiration station; immersion means for vertically moving the suction tube into and out of a vial at the station so as to immerse a lower end of the tube in the liquid in such vial; flow means for withdrawing liquid in the vial for the subsequent processing of at least a portion of the withdrawn liquid; and means carried by the aspirator for agitating the liquid in the vial at the aspiration station prior to the withdrawal of the liquid from the vial.

2. Apparatus according to claim 1 wherein the agitating means comprises a rotary mixer.

3. Apparatus according to claim 2 wherein the mixer comprises a tubular member concentric with the suction tube, means for rotating the tubular member about its axis, and means for maintaining the suction tube stationary.

4. Apparatus according to claim 3 wherein the suction tube is disposed within the tubular member.

5. Apparatus according to claim 4 wherein the aspirator includes a frame, wherein the suction tube is fixedly mounted to the frame, and including means for rotatably mounting the tubular member to the frame.

6. Apparatus according to claim 5 wherein the tubular member has a lower end protruding past a corresponding end of the suction tube.

7. Apparatus according to claim 6 wherein the lower end of the tubular member is defined by a cylindrical wall, and including at least one downwardly opening groove in the cylindrical wall to facilitate the agitation of the liquid in the vial.

8. Apparatus for sequentially aspirating a liquid from a plurality of upwardly open vials for the subsequent individual processing of aspirated liquid from each vial comprising: an aspirator including an upright, downwardly opening suction tube for sequential insertion into the vials, tray means supporting the vials for incrementally moving the vials to an aspiration station; positioning means for aligning the suction tube and the vial at the aspiration station; immersion means for vertically moving the suction tube into and out of a vial at the station so as to immerse a lower end of the tube in the liquid in such vial, the immersion means comprising an upright rod having an upper end to which the aspirator is mounted, and means for vertically reciprocating the rod so that the lower end of the suction tube is above an upper end of the vial at the aspiration station when the rod is in its raised position and immersed in the liquid and proximate but spaced from a bottom of the vial when the rod is in its lowered position; and flow means for withdrawing the liquid in the vial for the subsequent processing of at least a portion of the withdrawn liquid.

9. Apparatus according to claim 8 including first drive means for vertically reciprocating the rod comprising a rack and pinion drive including a load reversible electric motor for rotating the pinion of the drive and for reversing its rotational direction whenever the rod encounters a torque of a predetermined magnitude which opposes the continued movement of the rod in a given direction; whereby misalignments and an interference between the suction tube and objects including the vial at intermediate positions of the reciprocating rod automatically terminates further movement of the rod and of the suction tube in such direction and thereby prevents damage to the apparatus and the vial.

10. Apparatus according to claim 9 including optical limit switches operatively electrically coupled with the electric motor for sensing raised and lowered positions of the rod and for de-energizing the electric motor in response to sensing the presence of the rod in either one of said positions to prevent further travel of the rod in a given direction.

11. Apparatus for sequentially aspirating a liquid from a plurality of upwardly open vials for the subsequent individual processing of aspirated liquid from each vial comprising: an aspirator including an upright, downwardly opening suction tube for sequential insertion into the vials; tray means supporting the vials for incrementally moving the vials to an aspiration station; positioning means for aligning the suction tube and the vial at the aspiration station; immersion means for vertically moving the suction tube into and out of a vial at the station so as to immerse a lower end of the tube in the liquid in such vial; flow means for withdrawing the liquid in the vial for the subsequent processing of at least a portion of the withdrawn liquid; and a container holding a rinsing solution for rinsing the interior and the exterior of the suction tube after the liquid in the vial has been withdrawn to prevent contamination of the liquid in the next vial to be aspirated by the liquid from the previously aspirated vial; the positioning means including means for aligning the suction tube with the container; and the immersion means including means for vertically moving the suction tube into and out of the container when the container and the tube are in alignment.

12. Apparatus according to claim 11 wherein the tray means includes a tray having means for holding the vials, and means for moving the tray along a predetermined path past the aspiration station, and wherein the positioning means includes means for arresting movement of the tray means when a vial is at the aspiration station.

13. Apparatus according to claim 12 wherein the tray means includes means for rotating the tray about an axis and means for mounting the vials to the tray in a general circular pattern concentric with respect to the tray axis, and wherein the tray moving means comprises means for rotatably moving the tray in fixed increments about its axis so as to present a vial at the aspiration station after an incremental movement of the tray.

14. Apparatus according to claim 12 wherein the vial holding means includes means for arranging the vials in a plurality of concentric, radially spaced rows; and wherein the positioning means includes means for moving the suction tube in a direction transverse to the direction of movement of the vials past the aspiration station into alignment with a plurality of vials which equals the plurality of rows while the tray remains stationary.

15. Apparatus according to claim 14 wherein the means for moving the suction tube comprises a frame for mounting the tube and means for pivoting the frame about an aspirator axis parallel to the suction tube between a first position in which the tube is aligned with a vial at the station in a first row and a second position in which the tube is in alignment with a vial at the station in the second row.

16. Apparatus according to claim 15 wherein the vial mounting means includes means arranging the vials at the aspiration station so that centers of such vials substantially lie on a circularly arcuate line having as its origin the aspirator axis.

17. Apparatus according to claims 16 wherein the container is positioned on the arcuate line, and wherein the means for aligning the suction tube with the container comprises means for pivotally moving the frame about the aspirator axis until the suction tube is in substantial alignment with the container.

18. Apparatus according to claim 17 wherein the positioning means includes second drive means for pivotally moving the frame about the aspirator axis, the second drive means including signal means for indicating when the tube is in alignment with any one of the container and the vials at the aspiration station, the means responsive to the signal means for arresting the pivotal movement of the frame when the suction tube is in alignment with a vial or the container into which the suction tube is to be moved.

19. Apparatus according to claim 18 wherein the immersion means includes first drive means having an upright rod connected with the aspirator, the rod being aligned with and mounted to rotate about the aspirator axis; and wherein the second drive means includes a crank drive operatively coupled with the rod and having a drive wheel, the crank drive being arranged so that one rotation of the drive wheel causes a pivotal movement of the frame and therewith of the suction tube from a given point along said arcuate line over all other points on said line and back to said given point.

20. Apparatus for sequentially aspirating a liquid from a plurality of upwardly open vials for the subsequent individual processing of aspirated liquid from each vial comprising: as aspirator including an upright, downwardly opening suction tube for sequential insertion into the vials; tray means supporting the vials for incrementally moving the vials to an aspiration station, and including vial holding means arranging the vials in at least one circular row, means mounting the vial holding means for rotation about an upright tray axis so that rotation of the vial holding means sequentially presents the vials at the aspiration station, and a notched index wheel fixedly connected with the vial holding means and rotatable therewith, the index wheel having a number of notches corresponding to the number of positions of the vial holding means at which a vial is presented at the aspiration station; positioning means for aligning the suction tube and the vial at the aspiration station, the positioning means including a detent, and spring means resiliently biasing the detent into engagement with the notches, the detent being positioned so that a vial is aligned with the suction tube at the aspiration station when the detent fully rests in a corresponding notch in the index wheel; immersion means for vertically moving the suction tube into and out of a vial at the station so as to immerse a lower end of the tube in the liquid in such vial; and flow means for withdrawing liquid in the vial for the subsequent processing of at least a portion of the withdrawn liquid.

21. Apparatus according to claim 20 wherein the tray means includes third drive means operatively engaging the index wheel for incrementally advancing the index wheel to subsequentially engage the notches on the index wheel with the detent.

22. Apparatus according to claim 21 wherein the notches in the index wheel are radially oriented, and wherein the detent is biased towards the index wheel in a radially inward direction.

23. Apparatus according to claim 21 wherein the third drive means comprises drive pin means having a surface shaped to engage the notches in the index wheel and mounted adjacent of the index and means for moving the surface to engage a notch on the index wheel and rotatably advance the index wheel to engage the detent with another notch and to thereby align another vial with the suction tube at the aspiration station.

24. Apparatus according to claim 23 wherein the cam surface is eccentrically mounted to a rotatable cam wheel, and including means for resiliently biasing the surface towards the index wheel, the means limiting the extent to which the surface can move towards the index wheel so that the surface engages the index wheel during only a portion of the rotation of the cam wheel.

25. Apparatus according to claim 24 wherein the third drive means includes means for rotating the cam wheel through one full revolution for rotatably advancing the index wheel through an arc no greater than the arc between adjoining notches.

26. Apparatus for retrieving liquid samples from a multiplicity of relatively long, upright, upwardly open vials for the subsequent independent processing of each sample comprising: a vial holder holding the vials in an upright position and arranging the vials in at least one row; advancing means for moving the vial holder to present each vial at an aspiration station; an aspiration including a frame, a vertically oriented suction tube fixedly mounted to the frame, and means for connecting the suction tube to a vacuum source; an upwardly open container spaced from the rows and located proximate the aspiration station for holding a volume of a rinsing solution; positioning means for moving the frame to alternatively substantially vertically align the suction tube with a vial at the aspiration station and with the container; immersion means for raising and lowering a lower end of the suction tube between a raised position at which the lower suction tube end clears an upper end of the vial at the aspiration station and the container and a lowered position at which the lower suction tube end is immersed in liquid in the tube or the container; means arranged so as to prevent the operation of the positioning means when the lower suction tube end is at a vertical position lower than the uppermost end of the vial at the aspiration station and the container; and means for operating the positioning means and the immersion means so as to immerse the suction tube in the container after each immersion of the suction tube in a vial at the aspiration station.

27. Apparatus according to claim 26 including a rotary mixer arranged concentrically about the suction tube for mixing the liquid in the vial preparatory to its withdrawal therefrom.

28. Apparatus according to claim 26 including indexing means for positioning the vial at the aspiration station, the indexing means being independent of the advancing means.

29. Apparatus according to claim 26 wherein the vial holder arranges the vials in at least two side by side, parallel rows; wherein the frame moving means includes means for pivoting the frame about an upright frame axis so that the suction tube moves along a circularly arcuate path; and wherein a vial in each row is simultaneously positioned at the aspiration station.

30. Apparatus according to claim 29 wherein the vials at the aspiration station and the container are located along a circularly arcuate line which has its origin at the frame axis and a radius substantially equal to the distance between the frame axis and the axis of the suction tube.

31. Apparatus according to claim 26 wherein the vial holder arranges the vials in a plurality of rows; and including means for aligning a vial in each row with the aspiration station, the aligning means comprising an index member fixedly attached to the vial holder for movement therewith, a detent biased towards the indexing member, the indexing member and the detent defining cooperating concave and convex index surfaces, the surfaces being arranged so that upon the mutual engagement of the detent with a corresponding surface on the indexing member a vial in each row is aligned with the aspiration station, the number of surfaces on the indexing means being equal to the number of vials held by the holding means divided by the number of rows.

32. Apparatus for withdrawing from a multiplicity of upright vials a liquid for the subsequent independent testing of liquid from each vial comprising: a vial holder arranging the vials in at least one row of a predetermined shape and maintaining the vials in an upright position so as to render them accessible from the top; means for intermittently moving the holder parallel to the row to sequentially position the vials at an aspiration station; a container located proximate the aspiration station for holding a rinsing solution; an aspirator frame including at least a portion disposed above uppermost ends of the vials at the aspiration station and an uppermost end of the container; a suction tube affixed to the frame and having an open lower end and means for communicating the tube with a vacuum source; a rotary mixer secured to the frame proximate the tube and depending from the tube to a point below the lower tube end, the tube and the mixer being constructed so that they can be simultaneously inserted in a vial; immersion means for reciprocating the frame in a vertical direction over a sufficient distance so that in a raised position of the frame the lower end of the mixer is above the vials and the container and in a lowered position of the frame the lower end of the mixer and the lower end of the tube are immersed in liquid in the vial or the container; positioning means for moving the frame along a predetermined path to alternatively substantially align the tube and the mixer with a vial at the aspiration station and with the container; and means for sequentially energizing the holder moving means, the positioning means, the immersion means, and the mixer so that when the tube and the mixer are immersed in the liquid in a vial at the aspiration station, the mixer mixes the liquid prior to its withdrawal from the vial through the tube, thereafter the tube and the mixer are withdrawn in an upward direction from the vial and are moved into registration with the container, are immersed in the container to remove from the tube and the mixer substantially all liquid from the vial adhering thereto before the mixer and the tube are again aligned with another vial at the station and immersed in the liquid therein, whereby the liquid in the vials is uniformly mixed before its withdrawal therefrom and a cross-examination between liquids in different vials is prevented.

* * * * *